United States Patent [19]

Celio et al.

[11] 4,390,280

[45] Jun. 28, 1983

[54] ILLUMINATION CONTROL FOR A DENSITOMETER AND DENSITY MEASURING DEVICE HAVING SUCH CONTROL

[75] Inventors: Tino Celio, Ambri; Hans Ott, Regensdorf, both of Switzerland

[73] Assignee: GRETAG Aktiengesellschaft, Regensdorf, Switzerland

[21] Appl. No.: 190,572

[22] Filed: Sep. 25, 1980

[30] Foreign Application Priority Data

Sep. 28, 1979 [CH] Switzerland ................. 8792/79

[51] Int. Cl.³ .................. G01N 21/01; H05B 37/02; H05B 39/02
[52] U.S. Cl. ................................. 356/445; 315/307; 315/360
[58] Field of Search ................ 356/445–448, 356/369, 237, 231; 315/106, 307, 360

[56] References Cited

U.S. PATENT DOCUMENTS

| | | | |
|---|---|---|---|
| 3,653,764 | 4/1972 | Schodl | 250/554 |
| 3,868,540 | 2/1975 | Passmore et al. | 315/106 |
| 4,078,858 | 3/1978 | Mast | 356/446 |

FOREIGN PATENT DOCUMENTS 2038603 8/1970 Fed. Rep. of Germany.
2414277 8/1979 France.

OTHER PUBLICATIONS

Sanford, J. L., "Voltage Regulator with Precision Current Limiting", IBM Tech. Disclosure Bulletin, vol. 21, No. 11, Apr. 1979.

Primary Examiner—Bruce Y. Arnold
Attorney, Agent, or Firm—Burns, Doane, Swecker & Mathis

[57] ABSTRACT

A measuring instrument, such as a densitometer, that uses an incandescent lamp as a measuring light source is provided with a control stage for energizing the light source upon switch-on to prevent overshoot of the desired luminous flux from the lamp that occurs if the final energizing voltage is applied immediately. The control stage includes an amplifier with a negative feedback network that is fed with a reference voltage via a switch. The feedback network includes a resistance-capacitance element and is responsive to closure of the switch to establish the initial lamp energizing voltage at 1–2% below its final value and to allow the voltage to rise to its final value over a period of 1 to 3 seconds.

7 Claims, 2 Drawing Figures

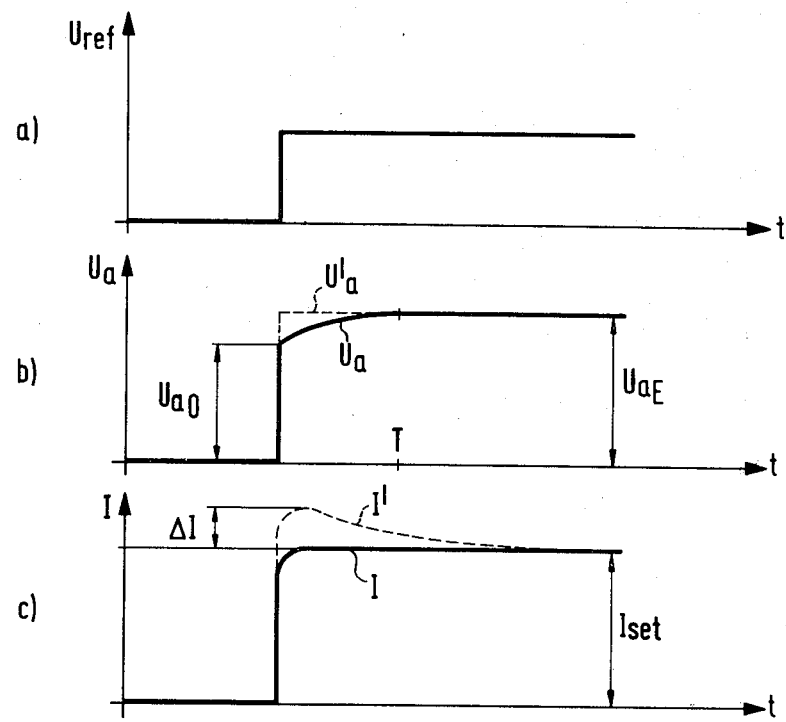

ILLUMINATION CONTROL FOR A DENSITOMETER AND DENSITY MEASURING DEVICE HAVING SUCH CONTROL

FIELD OF THE INVENTION

This invention relates to measuring apparatus, such as a densitometer, which makes measurements with the aid of light derived from an incandescent lamp source. The invention more generally relates to an illumination control system for such an instrument. The invention is concerned with avoiding false measurements that may arise due to the tendency to overshoot in the emitted light flux when an incandescent lamp is switched on to its full supply voltage and the invention is particularly concerned with a control means for avoiding such overshoot.

BACKGROUND TO THE INVENTION

In a modern densitometer, the light source usually consists of an incandescent lamp supplied with a constant voltage. The lamp is switched on immediately before each measurement and switched off immediately after the measurement. This intermittent lamp operation is for various reasons, including the saving of energy in battery-operated devices and for reducing the wear and increasing the life of the lamp. It has been observed that in the case of intermittent operation the luminous flux from the lamp does not remain constant in time in the period immediately following switch on. Immediately after the constant voltage has been switched on, the flux rises a few percent above the final desired value and then slowly falls to the constant set value during a relatively long time, up to a second or more. This overshooting of the luminous flux results in errors in linearity when photo-electrically measuring the object under test, and these errors cannot be compensated by the measuring circuit itself. The reason is that if, as is common today, the measurement process includes an integration method with variable integration period, the overshooting luminous flux affects the result to a varying extent, depending on the integration period.

Theoretically, of course, the aforementioned error in linearity could be eliminated by adjusting the lamp voltage to obtain a constant luminous flux from the moment of switch on. However, such an adjustment would require an additional photodetector and a complicated regulating circuit. This is undesirable in terms of cost and often impossible for lack of space or other reasons.

Another possibility of reducing or eliminating the overshoot of the luminous flux would of course be to switch the lamp on permanently or permanently preheat it at a reduced voltage. As already mentioned, however, this method is disadvantageous with regard to energy consumption and the life of the lamp.

The protection of an incandescent lamp to extend its life in a measuring instrument is described in German Offenlegungschrift No. 2 038 603 which relates to a reflection photometer and discloses a lamp which is protected by being operated at a considerably reduced voltage. A colorimeter type measuring instrument having an intermittently operated lamp is disclosed in U.S. Pat. No. 3,653,764 to Schodl. In this case the light colour as well as intensity is of importance. The lamp is protected at each switching on by being operated initially at constant current and then at constant voltage. A blanking gate system is provided to ensure the measuring signal obtained with the aid of the lamp is transmitted only during the latter portion of the switch on period when the light flux is essentially constant. Such measures are relatively complex.

It is also known to preserve incandescent lamps for airport lighting systems by having a control system for "gently" switching them on. Such a system is disclosed in French laid-open patent specification No. 2 414 277. The disclosed control system provides on switch on a continuous increase in voltage to the lamps rising slowly from zero to the rated value. As can be seen from FIG. 2 of the French specification, the period of the rising voltage is long and is too long for practical use in an instrument such as a densitometer.

It is, therefore, an object of the present invention to provide a means for controlling the energisation of an intermittently operable incandescent lamp in a densitometer or like measuring instrument whereby overshoot of the luminous flux above the set level is avoided on switching on, and further to provide such control means in a relatively simple and inexpensive manner.

SUMMARY OF THE INVENTION

In accord with one aspect of the invention there is provided an illumination control system for a densitometer or like measuring instrument using an incandescent electric lamp as a measuring light source, which system comprises a control stage for supplying energising voltage to the lamp; means for supplying the control stage with a reference voltage to set the energising voltage at a given constant value; and switch means connected to the control stage for switching on and off the supply of energising voltage thereby. Further in accord with the invention the control stage comprises means setting the relationship of the energising voltage to the reference voltage such that upon switch on the energising voltage assumes a value 1–2% less than the given constant value finally achieved and rises to the given constant value over a period in the range of 1–3 seconds.

The invention also provides in another aspect a measuring instrument, such as a densitometer, of the type that measures a property of an object under test with the aid of light derived via the object from an incandescent lamp, which instrument comprises: a control stage connected to the lamp to supply energising voltage thereto; means for supplying the control stage with a reference voltage to set the energising voltage at a given constant value; and switch means connected to the control stage for switching on and off the supply of energising voltage thereby. The control stage further comprises means setting the relationship of the energising voltage to the reference voltage such that upon switch on the energising voltage assumes an initial value 1–2% less than the given constant value to be finally achieved and rises to this latter value over a period such that overshoot of the luminous flux from the lamp above its final constant value is substantially prevented. To this end the period of voltage rise may lie in the range of about 1 to 3 seconds. The aforementioned setting means establishes the initial and final energising voltage values with respect to the reference voltage and the rise period and to this end preferably comprises an amplifier, for example a high gain operational amplifier, and a negative feedback network connected to the amplifier that includes a resistor-capacitor combination providing a time varying stage gain upon switch on.

The switch means is conveniently arranged between the reference voltage source and an input of the amplifier.

BRIEF DESCRIPTION OF THE DRAWINGS

The invention will now be explained in greater detail, with reference to an embodiment illustrated in the accompanying drawings, in which:

FIG. 2 shows in graphical form the variation with time (t) of various circuit voltages and the luminous flux from the lamp in the densitometer according to FIG. 1.

Figure 1:
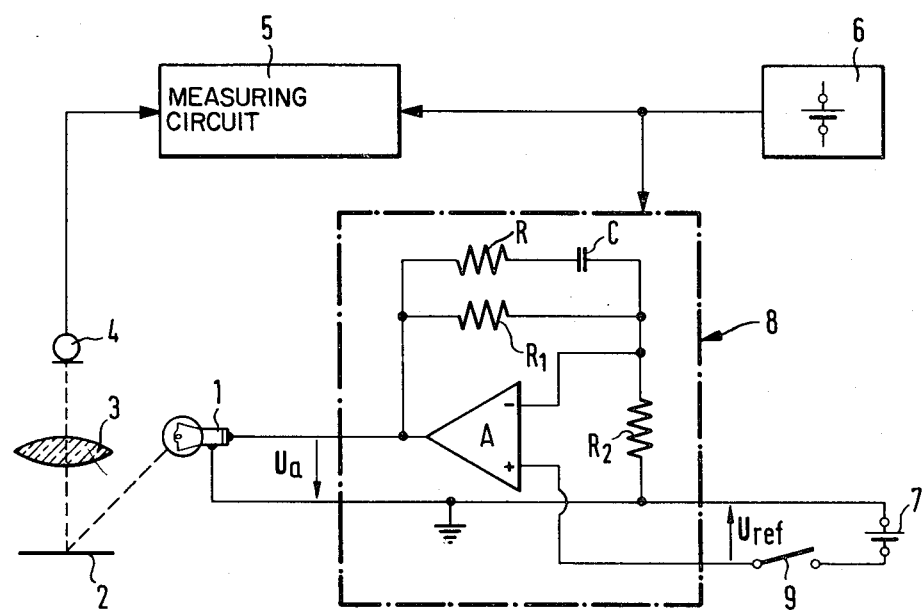
FIG. 1 is a block circuit diagram of a densitometer according to the invention.

The illustrated densitometer comprises an incandescent lamp 1 for illuminating an object 2 under test; an optical measuring system shown diagrammatically at 3; and a photoelectric transducer 4 to provide an electric signal that is a measure of the light from the object 2. The transducer signal is supplied to a measuring circuit 5 which includes an integration circuit of variable integration period as previously mentioned. The lamp 1 is supplied with an energisation voltage $U_a$ set with reference to a reference voltage $U_{ref}$ obtained from a reference voltage source 7. The energisation voltage is supplied by a control stage 8 under the control of a switch 9 for actuating lamp 1, i.e. switching it on and off by switching on and off the reference voltage applied to the control stage. A power supply 6 provides power to the circuit. Except for the control stage 8, the illustrated densitometer is substantially the same in construction as conventional densitometers and therefore need not be described in detail. The lamp and optical head of a comparable densitometer is described, for example, in U.S. Pat. No. 4,078,858. Densitometers having the general circuitry shown may be obtained from Messrs. Gretag AG of Regensdorf, Switzerland, under the model designations D 122 and D 300.

In accord with this invention the control stage 8 provides a particular control of the energisation voltage $U_a$ in response to the application to the stage of reference voltage $U_{ref}$ upon closure of switch 9. To this end stage 8 comprises an amplifier A of high internal gain and a negative feedback network comprising three resistors R, $R_1$, $R_2$ and a capacitor C supplying a feedback voltage to the inverting input (−) of amplifier A whose non-inverting input (+) receives the voltage from source 7 via switch 9. The overall gain of the control stage is set by the feedback network and its operation is analysed more fully hereinafter. For the moment it will suffice to say that the quiescent or static state gain is set by $R_1$ and $R_2$ and that the resistor R and capacitor C shunting resistor $R_1$, are effective to modify (reduce) the gain under transient conditions such as at switch on.

Referring now to FIG. 2 in conjunction with FIG. 1, on account of the negative-feedback capacitor C, when the reference voltage $U_{ref}$ is applied by switch 9 to the non-inverting input of amplifier A (FIG. 2 - curve (a)), the amplifier output voltage $U_a$ does not immediately jump to the constant end value $U_{aE}$ (FIG. 2 - curve (b)) but to an initial value $U_{ao}$ which is 1 to 2% less, from which it continuously rises for a period of about 1 to 3 seconds to substantially the end value $U_{aE}$. The variation in the output voltage $U_a$ is shown graphically in full line in FIG. 2 - curve (b). For clarity of illustration, the difference between the initial voltage $U_{aO}$ and the final voltage $U_{aE}$ is greatly exaggerated in the graph.

Curve (c) of FIG. 2 shows in full line the variation with time of the luminous flux or light intensity I of the incandescent lamp 1 operated at a voltage $U_a$ varying as shown in full line in curve (b). As shown by the continuous line, the intensity I is at the set value $I_{set}$ substantially immediately after the lamp has been switched on, and does not overshoot. If lamp 1 was operated to have the full voltage $U_{aE}$ applied to the lamp immediately after switching on (as shown by the broken line $U_a'$ in curve (b)), the intensity would overshoot by $\Delta I$ or approximately 4-8% above the set value $I_{set}$ (as shown by the broken line I' in curve (c) of FIG. 2).

In the embodiment in FIG. 1, the output voltage $U_a$ has the formula:

$$U_a = \alpha \cdot U_{ref}(1 - K \cdot \exp(-t/\tau))$$

In this formula:

$$\alpha = \left(1 + \frac{R_1}{R_2}\right)$$

$$K = \frac{R_1}{R_1 + R_2} \cdot \frac{R_1}{R_1 + R}$$

$$\tau = R \cdot C$$

The parameters $\alpha$, K and $\tau$ are empirically determined for each lamp for optimum compensation of the overshoot. The following are practical values of $\alpha$, K and $\tau$ for a Zorn 0501241 type 1.5 W lamp.

$$\alpha = 2; K \approx 0.015; \tau \approx 0.6 \text{ sec.}$$

These parameters may be realised with the following feedback element values: $R_1 = R_2 = 56$ KΩ; $R = 1.8$ MΩ; $C = 0.33$ μF.

In the described example, the negative-feedback network has only one RC shunt element. If required, of course, a number of RC elements can be provided, so that the variation in output voltage $U_a$ can always be chosen in optimum manner. The circuit parameters are chosen such that the voltage $U_a$ essentially achieves its end or final constant value at a time, such as T in FIG. 2 - curve (b) that lies in the range of 1-3 seconds after switch on.

Although the amplifier A is shown as energising lamp 1 directly, in practice it is more likely that the control stage would comprise a power amplifier energising the lamp and controlled by the high gain operational amplifier A having its stage gain set by the feedback network as described.

The above described control stage 8 for lamp 1 is particularly simple and requires practically no additional expenditure as compared with conventional constant-voltage lamp control systems. This is because the source 7 of reference voltage $U_{ref}$ and the amplifier A are required in any case for producing a constant supply voltage to the lamp, so that the extra expenditure for compensating overshoot is restricted to an RC element (resistor R and capacitor C).

What is claimed is:

1. An illumination control system for measuring instruments of the type that measure a property of an object under test with the aid of light derived via the object from an incandescent electric lamp as a source of measuring light, comprising:
   a control stage for supplying energizing voltage to the lamp;

means for supplying the control stage with a reference voltage to set the energizing voltage at a given, constant, final value; switch means connected to the control stage for switching on and off the supply of energizing voltage thereby;

wherein said control stage includes means which sets the relationship of the energizing voltage to the reference voltage such that, upon said switch being turned to the "on" position, the energizing voltage assumes a value 1–2% less than said given, constant, final value and then rises to said given, constant, final value over a period of about 1 to 3 seconds.

2. An illumination control system as claimed in claim 1, in which said control stage comprises an amplifier and a negative feedback network connected to said amplifier to set the stage gain thereof,, said feedback network including a resistor-capacitor combination providing a time-varying stage gain upon said switch being turned to the "on" position.

3. An illumination control system as claimed in claim 2 in which said switch means is connected between said means for supplying the control stage with a reference voltage and an input of said amplifier.

4. A measuring instrument of the type that measures a property of an object under test with the aid of light derived via the object from an incandescent electric lamp, the measuring instrument further comprising:

a control stage connected to the lamp to supply energizing voltage thereto;

means for supplying the control stage with a reference voltage to set the energizing voltage at a given, constant, final value;

switch means connected to the control stage for switching on and off the supply of energizing voltage thereby;

wherein said control stage includes means which sets the relationship of the energizing voltage to the reference voltage such that, upon said switch being turned to the "on" position, the energizing voltage assumes an initial value 1–2% less than said given, constant, final value and then rises to said given, constant, final value over a period of about 1 to 3 seconds.

5. A measuring instrument as claimed in claim 4 in which said setting means comprises an amplifier and a negative feedback network connected to the amplifier including a resistor-capacitor combination providing a time varying stage gain upon said switch being turned to the "on" position.

6. A measuring instrument as claimed in claim 5 in which said switch means is connected between said means for supplying the control stage with a reference voltage and an input of said amplifier.

7. A measuring instrument as claimed in claim 5 in which said property of an object under test is measured with the aid of a transducer responsive to the light from the object under test to provide an electrical signal representing the intensity of said light beam from the object and a measuring circuit responsive to said electrical signal, and wherein said measuring circuit includes means for integrating said electrical signal.

* * * * *